(12) United States Patent
Groke et al.

(10) Patent No.: US 7,855,191 B2
(45) Date of Patent: Dec. 21, 2010

(54) AGENT HAVING A DESTRUCTIVE EFFECT ON MALIGNANT TUMORS AND METHOD FOR THE PRODUCTION THEREOF

(75) Inventors: Karl Groke, Eggersdorf bei Graz (AT); Ilse Groke, legal representative, Eggersdorf bei Graz (AT); Veronika Groke, legal representative, Eggersdorf bei Graz (AT); Paul Groke, legal representative, Eggersdorf bei Graz (AT); Ralf Herwig, Westendorf (AT); Peter Ferdinand, Hans-Fritz-Weg 26, A-8043 Graz (AT)

(73) Assignees: C.Y.L. Pharmazeutika GmbH, Lieboch (AT); Peter Ferdinand, Graz (AT)

( * ) Notice: Subject to any disclaimer, the term of this patent is extended or adjusted under 35 U.S.C. 154(b) by 988 days.

(21) Appl. No.: 10/536,777

(22) PCT Filed: Oct. 13, 2003

(86) PCT No.: PCT/EP03/50712

§ 371 (c)(1),
(2), (4) Date: Sep. 7, 2006

(87) PCT Pub. No.: WO2004/047832

PCT Pub. Date: Jun. 10, 2004

(65) Prior Publication Data

US 2006/0292218 A1 Dec. 28, 2006

(30) Foreign Application Priority Data

Nov. 27, 2002 (AT) .............................. A 1778/2002

(51) Int. Cl.
*A61K 31/33* (2006.01)
*A61K 31/34* (2006.01)

(52) U.S. Cl. ...................................... 514/183; 514/461

(58) Field of Classification Search ................. 514/183, 514/461
See application file for complete search history.

(56) References Cited

U.S. PATENT DOCUMENTS 5,006,551 A * 4/1991 Groke et al. ................ 514/461

FOREIGN PATENT DOCUMENTS

EP 0 326 826 8/1989

OTHER PUBLICATIONS

Peckham et al 'Oxford Texbook of Oncology' Oxford University Press, vol. 1, p. 451, 1995.*
Menter et al 'Selenium Effects on Prostate cell growth' Cancer Epidemiology, Biomarkers and Prevention, vol. 9, p. 1171-1182, 2000.*
Bommarius 'L-methionine and related L-amino acids by acylase cleavage of their corresponding N-acetyl-DL-derivatives' Tetrahedron, vol. 8 (19), p. 3197-3200, 1997.*
Millis et al 'Growth inhibition of subcutaneously transplanted hepatomas without cachexia by alteration of the dietary arginine-methionine balance' Nutrition and Cancer, 31(1), p. 41-55, 1998.*

* cited by examiner

*Primary Examiner*—Brandon J Fetterolf
*Assistant Examiner*—Christopher R Stone
(74) *Attorney, Agent, or Firm*—Jonathan Myers

(57) ABSTRACT

Disclosed is an agent which has a destructive effect on malignant tumors and contains alpha-ketoglutaric acid, N-acetyl-seleno-L-methionine, N-acetyl-L-methionine, and a compound that is capable of forming azomethine and is selected among the group 5-hydroxymethylfurfural, dehydroascorbic acid, maltol, and vanillin as an active substance, 5-hydroxymethylfurfural being preferred. The inventive agent can be used in the form of an infusion, in an oral or rectal form of administration, or as an irrigation in cancer therapy.

21 Claims, No Drawings

AGENT HAVING A DESTRUCTIVE EFFECT ON MALIGNANT TUMORS AND METHOD FOR THE PRODUCTION THEREOF

CROSS REFERENCE TO RELATED APPLICATIONS

This application is the US national phase of PCT application PCT/EP2003/050712 filed 13 Oct. 2003 with a claim to the priority of Austrian patent application A1778/2002 itself filed 27 Nov. 2002.

TECHNOLOGICAL FIELD

The present invention relates to an agent [composition, product] with a destructive [cytocidal] effect on malignant tumors and which has as its effective component alphaketoglutaric acid [α-ketoglutaric acid] or a pharmaceutically acceptable salt thereof and at least one compound capable of forming azomethine in an enzyme-independent reaction selected from the group which consists of 5-hydroxy-methylfurfural, dehydroascorbic acid, maltol and vanillin, and whereby preferably the mass ratio [weight ratio] of the ketoglutaric acid to the at least one compound capable of forming azomethine is greater than 1:1 and is, especially, 2:1 to 12:1.

STATE OF THE ART

Such a composition has been described in European patent EP 326826 B1.

It is known that in a series of patients with malignant tumors, a highly significant increase of alpha-ketoglutaric acid in the blood can be found. This increased blood level is a result of a disturbance in the citric acid cycle in the tumor cells which leads to enrichment of alpha-ketoglutaric acid in the tumor. Since the alpha-ketoglutaric acid is detrimental to the tumor because of its high pH value, this acid exudes from the tumor in increased amounts and the presence of ammonia or amines can promote this effect.

The effectiveness of the agent or composition described in European patent EP 326826 B1 is based upon the fact that alpha-ketoglutaric acid in higher concentrations will destroy tumor cells. It is not however sufficient to supply α-ketoglutaric acid to the tumor. Rather, one must suppress the exudation of the α-ketoglutaric acid from the tumor to the greatest possible extent. Therefore, the effective agent should contain not only α-ketoglutaric acid so that in spite of its depletion, the blood level thereof in the tumor is increased, but further effective substances which can bind ammonia and amines in enzyme-independent reactions by the formation of azomethine and thus remove these compounds which contribute to the exudation or elimination of α-ketoglutaric acid so that the exudation of the alpha-ketoglutaric acid from the tumor is blocked. As such substances, 5-hydroxymethylfurfural, dehydroascorbic acid, maltol and vanillin have been named in European patent EP 326826 B1, whereby 5-hydroxymethylfurfural is especially preferred. The enrichment of the alpha-ketoglutaric acid in the tumor has the effect of so damaging the tumor that it can be completely eliminated. A prerequisite of this is that the malignant condition of the patient is accompanied by an increase in the alpha-ketoglutaric acid level in the blood. Clinical studies of the effect of the preparation are described in Austrian patent AT 393, 221 B1.

It is also known that selenium compounds can have a beneficial effect upon patients with certain malignant pathologies. Thus, in the publication of A. Pakdaman in *Biol.-Trace-Elem-Res.* 1998 April-May; 62 (1-2) 1-6, the administration of a selenium compound, namely Na-selenite, to patients with malignant brain tumors, can give rise to an improvement in the general well-being of the patients as manifested by, among other things, in all patients treated, an improvement in the number of erythrocytes, an improvement in the hemoglobin value and an improvement in the thrombocyte count. 76% of these patients felt, in addition, a reduction in unpleasant side effects. The use of selenite has been found to be especially advantageous for those patients with brain tumors who benefit from oxygen therapy. Whether this medication also improves the cancer condition itself has not been determined. From the literature, it can be said as to selenium compounds that they serve primarily as cancer-preventative agents. They are not considered as therapeutically effective for the treatment of cancers, but rather as prophylaxis against cancer. They are provided mainly as food supplements and can be combined with herbs or vegetables. Thus in the literature combinations of them with, for example, garlic, onion or broccoli are mentioned.

Also concerned with cancer prophylaxis are Jian C., Jiang W., Ip Cl., Ganther H. And Lu J. in their work "Selenium-induced inhibition of Angiogenesis in Mammary Cancer at chemopreventative levels of intake". Molecular Carcinogenesis 26, 213-225, (1999).

In this work, it was researched whether the cancer prophylaxis was a consequence of the affect of selenium at least in part of a blockage of the angiogenesis associated with the occurrence of cancer. For this research, rats were used in which by the enrichment of 1-methyl-1-nitro urea, a mammary cancer had developed. In these rats a determination was made as to the density of microvascular in the carcinoma when the rats were given selenium in the form of garlic which had been enriched in selenium as the sodium sel or as selenium-methylselenocysteine. It then could be determined that the density of the intra tumoral microvessels in the mammary carcinoma were significantly reduced.

With respect to the substance Se-methylselenocystein, no details as to the method of making the compound were given but it was only indicated that this substance constituted a component by which the selenium was provided in the selenium-enriched garlic. From these investigations, which were carried out in vitro and in vivo, it was found that the selenium appeared to have an antiangiogenic activity which contributed to a cancer prophylaxis.

In order to optimize the preparation described in European Patent EP 326826 B1, the inventors of the present application, relying upon the Jiang C. et al publication cited above, have relied upon the antiangiogenic effect of selenium compounds in parallel with the agent according to the above cited patent, for the case of cancer conditions in which the density of microvessels can be reduced to limit the blood supply for a tumor.

DISCLOSURE OF THE INVENTION

Since the inventors of the present invention have recognized that the antiangiogenic activity of selenium compounds can also contribute a mechanism for destruction of the tumor, they have investigated whether the effect of the selenium compounds is also applicable to other cancers and will or will not result in a disruption of the angiogenesis in such tumors. A further investigation was made into the form in which selenium could be added to the preparation according to European Patent EP 326826 B1.

Thus initially the research was carried out by the addition of selenium in the form of selenite. This substance however was found not to be suitable because upon its addition there was immediately a reaction between the alpha-ketoglutaric acid and the selenite as a result of which amorphous selenium precipitated out. Attempts were made to suppress this redox reaction by incorporating the selenium in organic compounds. As such a compound, finally seleno-methionine was selected. Investigation showed that this selenium compound does not react with the alphaketoglutaric acid. Research showed however that because of the free amino group of the seleno-methionine, this compound undergoes a Maillard reaction with the ketoglutaric acid which at the higher temperatures that are required for heat sterilization, is especially significant. Surprisingly it has been found that the substance N-acetyl-seleno-L-methionine satisfies all of the requirements with respect to compatibility with the alphaketoglutaric acid. However, with the addition of this compound as a complement to the composition of European Patent 326826 B1 there is a danger that this substance will be incorporated into body proteins, and effect which might reduce the desired effect of the N-acetyl-seleno-L-methionine or cause the effect of that compound to be completely lost. However, it has been surprisingly found that with the addition to the composition of N-acetyl-L-methionine in an amount which is about 100 times the amount of N-acetyl-seleno-L-methionine in protein is suppressed.

In research based upon the previous work with such compositions, it was found wholly unexpectedly that, under these conditions, the N-acetyl-seleno-L-methionine in conjunction with the effective substances of the composition from European Patent 326826B1 provides an increase in effectiveness which is beyond an additive effect and surprisingly is synergistic.

The subject of the present invention is, therefore, an agent or composition of the type described at the outset which contains as further effective substances, N-acetyl-seleno-L-methionine and N-acetyl-L-methionine whereby the latter is present in excess over the former.

The therapeutically effective agent according to the invention therefore contains at least four effective substances, namely, alpha-ketoglutaric acid, one or more compounds which contribute to azomethine formation with ammonia or amines present in the tumor and among other things serve to limit the exudation of alpha-keto-glutaric acid from the tumor, N-acetyl-seleno-L-methionine and N-acetyl-L-methionine. This composition is capable of reducing the exudation of α-ketoglutaric acid from the cancer tissue and thus producing a higher titer of this acid in the tumor tissue which finally can destroy the tumor. As a compound contributing to the azomethionine-5-hydromethyl furfural has been found to be especially effective.

It is advantageous when the mass of the weight ratio of the alpha-ketoglutaric acid to the N-acetyl-seleno-L-methionine is 100:1 to 20,000:1, preferably 500:1 to 10,000:1, and the mass or weight ratio of the N-acetyl-seleno-L-methionine to the N-acetyl-seleno-L-methionine is 20:1 to 300:1, preferably 50:1 to 100:1.

The N-acetyl-seleno-L-methionine is a substance which has been described in the literature and can be made as described by N. Karnbrock et al, Journal American Chemical Society (1996), 118 (4), 913-914 with good yield. A use of this substance as an effective agent in cancer therapy has not been described heretofore. Also another therapeutic indication has not been found.

The composition according to the invention has been found to have an especially good effect when the mass or weight ratio of the α-ketoglutaricacid to the substance promoting azomethine formation amounts to 2:1 to 12:1.

It has been found to be advantageous further to add to the compositions according to the invention a monosaccharide, especially glucose, fructose or a mixture thereof, since the acid metabolites thereof support the effect of the alpha-ketoglutaricacid on the malignant tumor and in addition also contribute a stabilizing effect to the anticancer agent. When the anticancer agent which is not to be supplied intravenously, instead of monosaccharides, also disaccharides can be added. These disaccharides also have a stabilizing effect and for the orally-administered compositions, also improve the taste.

Among the compounds which promote the azomethine formation, the 5-hydroxymethylfurferal has been found to e most suitable.

When the anticancer agent is provided in aqueous solution, the N-acetyl-seleno-L-methionine is preferably present in an amount of 1.4 to 2.3 mg/l and the N-acetyl-L-methionine in an amount of 70-230 mg/l. It is of no advantage, with a high amount of alpha-ketoglutaricacid, for example 16 g/l, to raise the quantity of the N-acetyl-seleno-L-methionine above the 2.3 mg/l level. Naturally the selenium compound will however be matched to the alpha-ketoglutaricacid in the preparation within the range of 1.4 to 2.3 mg/l. It amounts generally to about 0.1 weight or mass %. The amount of the N-acetyl-L-methionine used will be selected within the previously indicated limits based upon the amount of the seleno compound which is present.

The presence of high doses of α-ketoglutaricacid leads to a strongly acid reaction with the danger that the three other effective components of the preparation of the invention will be completely or partly decomposed and the effectiveness and stability detrimentally affected. It has thus been found to be advantageous to adjust the pH value of the agent according to the invention to a physiological range. Especially advantageous is a pH range of 4-6. In connection therewith it may be observed that the adjustment of the pH value by ammonia or an amine is excluded since these substances react with the oxogroup of the compounds promoting azomethine formation and the effectiveness of these compounds would thereby be suppressed.

For the adjustment of the pH value, by contrast, the addition of electrolytes from the group of sodium ions or potassium ions is highly preferred since the use of electrolytes in the solid state enables them to be supplied entirely or partly in the form of a mono salt with ketoglutaric acid.

The anticancer agent according to the present invention is preferably formulated as an intravenous formulation, especially in the form of an infusion.

With this formulation, an especially convenient and uniformly high blood level can be obtained which can apply its destructive effect to the entire tumor. This applies as well for such malignant pathologies in which the effective substances of the agent according to the invention can only be introduced into the tumor by the blood stream or in which the tumor can be flushed with blood. It is however possible to formulate the anticancer agent for an oral or rectal administration. This formulation is advantageous when the anticancer agent can be applied directly to the tumor through the intestinal tract.

If one is dealing with a pathology in an outwardly open body cavity, the therapeutic agent, according to the invention, can be applied also in the form of an irrigation.

As a rule, however, orally administrable formulations, such as capsules, tablets and also suspensions or solutions are used, as well as such therapeutic agents which are rectally administrable but not in the starting phase of therapy. These therapeutic forms are applied above all for the subsequent treatment of patients who have already undergone treatment with the therapeutic agent according to the invention, for example after such patients have gone home or are under house care. In addition, these therapeutic forms can be used for patients currently under treatment by infusion therapy on days in which the patient is in home care, usually on weekends and primarily in an oral formulation to bridge gaps in the administration of the medicament, especially where those gaps may have a negative effect on the blood level.

For the formulation of the therapeutic agent according to the invention as an infusion solution, the following composition has been found especially advantageous:

| | |
|---|---|
| alpha-ketoglutaric acid | 3–20 g/l |
| 5-hydroxymethylfurfural | 1–3 g/l |
| N-acetyl-seleno-L-methionine | 1.4–2.3 mg/l |
| N-acetyl-L-methionine | 70–230 mg/l |
| glucose | 20–100 g/l |
| sodium ion | 60–160 mmol/l |
| potassium ion | 15–40 mmol/l | whereby an infusion of the following composition:

| | |
|---|---|
| alpha-ketoglutaric acid | 6–16 g/l |
| 5-hydroxymethylfurfural | 1.0–2.5 g/l |
| N-acetyl-seleno-L-methionine | 1.4–2.3 mg/l |
| N-acetyl-L-methionine | 70–230 mg/l |
| glucose | 20–50 g/l |
| sodium ion | 70–160 mmol/l |
| potassium ion | 20–40 mmol/l | has been found to give especially good results. This applies especially in its use in the starting phase of administration of the medication. In the actual treatment phase the daily dosages used are, as a rule, 3 to 30 g alpha-ketoglutaric acid, 1 to 5 g 5-hydroxymethylfurfural, 1.4 to 2.3 mg N-acetyl-seleno-L-methionine and about 100 times that of N-acetyl-L-methionine.

For preparations which are formulated in solid or liquid form and orally or rectally administered, for example, in a gastro-intestinal pathology, it is desirable from the point of view of the pH value to have the ketoglutaric acid at least in part in the form of its mono-sodium salt or mono-potassium salt. The daily dosage of such a preparation will as a rule be somewhat lower than the dosage in the case of an infusion. The daily dosage thus may be at least 3 to 9 g $\alpha$-ketoglutaric acid and 0.5 to 1.5 g 5-hydroxymethylfurfural, 1.4 to 2.3 mg N-acetyl-seleno-L-methionine and 70 to 230 mg N-acetyl-L-methionine. The pH value for an orally administrable therapeutic agent lies below 4.

Further, for orally administrable forms of the preparation, the addition of glucose or a mixture of glucose and fructose is advantageous, although especially effective is the incorporation of a disaccharide, especially crude sugar, since an improvement in the taste can thereby be achieved.

For a subsequent treatment a still lower dosage can be chosen, for example the daily dosage of 2.25 g ketoglutaric acid and 0.375 g 5-hydroxymethylfurfural, 1.5 to 2.0 mg N-acetyl-seleno-L-methionine and 150 to 200 mg N-acetyl-L-methionine is preferred.

To produce the therapeutic agent according to the invention in a form suitable for intravenous administration, the $\alpha$-ketoglutaric acid is dissolved in a gas-treated low-oxygen water, the thus-obtained solution after possible addition of glucose or fructose and the addition of alkalis but not of ammonia or amine, is adjusted to a pH value of somewhat above 4 and to this mixture the N-acetyl-seleno-L-methionine, the N-acetyl-L-methionine and the compound for promoting azomethine formation are added. If the addition of glucose and/or fructose is contemplated, these compounds are supplied during the production of the infusion solution or together with the adjustment of the pH value.

In the case of the production of the therapeutic agent for oral or rectal administration, for the adjustment of the pH to 3 to 6, the ketoglutaric acid is in whole or in part introduced in the form of its monosalt with sodium or potassium and mixed with extenders and, if desired, also with disaccharides, whereupon the substance promoting azomethine formation, the N-acetyl-seleno-L-methionine and the N-acetyl-L-methionine are added. The mixture is then transformed into the desired dosage form, especially a beverage granulate, tablets or an irrigation liquid. With respect to the active ingredient promoting azomethine formation, care must be taken in its choice that the selected compound will not have a strong or unpleasant taste. In these respects as well, 5-hydroxymethylfurfural is the best choice.

BEST EMBODIMENTS OF THE INVENTION

In the following examples, detailed recipes are given for effective formulations of the therapeutic agent of the invention without the intention of thus limiting the present invention to them:

Example 1

| | |
|---|---|
| alpha-ketoglutaric acid | 6.000 g/l |
| 5-hydroxymethylfurfural | 2.000 g/l |
| N-acetyl-seleno-L-methionine | 1.5 mg/l |
| N-acetyl-L-methionine | 150 mg/l |
| glucose | 50.000 g/l |
| KOH (85%) | 1.320 g/l |
| NaOH | 1.200 g/l |

From these substances, a liter of a solution is prepared in which the ketoglutaric acid is initially dissolved in distilled water at a temperature of about 50° C., the water having previously been treated with gas and having a reduced oxygen content. NaOH and KOH are then introduced in succession into the resulting solution, as electrolytes, and glucose is added, and the pH is simultaneously set to slightly above 4. The thus-obtained clear solution then has the hydroxymethyl furfural and the two methionine derivatives added under stirring. One thereby obtains a clear, light-yellow solution which contains, per liter, 6 g of ketoglutaric acid, 2 g of 5-hydroxymethylfurfural, 1.5 mg of N-acetyl-seleno-L-methionine and 150 mg of N-acetyl-L-methionine as effective substances and, in addition, 50 g of glucose as well as electrolytes in the following molar concentrations:

| | |
|---|---|
| Na$^+$ | 30.00 mmol/l |
| K$^+$ | 20.00 mmol/l. |

The pH value of the solution amounted to 4.90. The solution had a calculated osmolarity of 385 mosmol/l of solution. It was put up as an infusion solution in bags of ½ liter capacity.

Example 2

| | |
|---|---|
| alpha-ketoglutaric acid | 16.000 g/l |
| 5-hydroxymethylfurfural | 2.000 g/l |
| N-acetyl-seleno-L-methionine | 2.3 mg/l |
| N-acetyl-L-methionine | 200 mg/l |
| glucose | 20.000 g/l |
| KOH (85%) | 1.650 g/l |
| NaOH | 4.000 g/l |

As described in Example 1, 1 liter of a solution was prepared from the above-mentioned substances which, apart from 16 g ketoglutaric acid, 2.3 mg N-acetyl-seleno-L-methionine, 200 mg N-acetyl-L-methionine and 2 g 5-hydroxymethylfurfural, contained 20 g glucose and electrolytes in the following molar concentrations:

| | |
|---|---|
| $Na^+$ | 160.00 mmol/l |
| $K^+$ | 25.00 mmol/l. |

The pH value of the solution amounted to 4.1. The calculated osmolarity was 362 mosmol/l of solution. The solution was put up in infusion bags of a capacity of ½ liter.

Example 3

| | |
|---|---|
| alpha-ketoglutaric acid | 12.000 g/l |
| 5-hydroxymethylfurfural | 2.000 g/l |
| N-acetyl-seleno-L-methionine | 2.0 mg/l |
| N-acetyl-L-methionine | 150 mg/l |
| glucose | 20.000 g/l |
| KOH (85%) | 1.320 g/l |
| NaOH | 4.000 g/l |

As described in Example 1, a 1 liter solution of these substances is prepared in which the ketoglutaric acid and 5-hydroxymethylfurfural effective substances are in a ratio of 6:1. Further, electrolytes in the following molar concentrations are added:

| | |
|---|---|
| $Na^+$ | 100.00 mmol/l |
| $K^+$ | 20.00 mmol/l. |

The pH value of the solution amounted to 4.68. The solution was put up in infusion bags of a capacity of ½ liter.

Example 4

345.12 g alpha-ketoglutaric acid mono-Na salt, 150 mg N-acetyl-seleno-L-methionine, 7.5 g N-acetyl-L-methionine and 1.190 g sifted sugar were dry mixed in a planetary mixer and passed through a sieve with a mesh width of 0.7 mm. The thus-obtained material was returned to the mixer and while the mixer was running, 100 gt of distilled water was added and mixing continued to agglomerate formation. After drying at 50° C., the product was granulated through a sieve of 1.25 mm mesh width and mixed in a planetary mixer with 50.0 g of 5-hydroxymethylfurfural. The pH value amounted to about 3. 1600 g of a mass were obtained which could be used as a drink granulate. It was put up in portion bags each containing 4 g. Each portion bag contained 0.75 g ketoglutaric acid, 0.125 g hydroxymethylfurfural as well as 0.375 mg N-acetyl-seleno-L-methionine and 18.75 mg N-acetyl-L-methionine.

Example 5

The same substances as in Example 4 with the difference, however, that instead of the saccharose, conventional lubricants and dispersants are incorporated and the composition worked up to tablets and then coated with a coating capable of resisting intestinal juices. The tablets can be used for the treatment of small intestine cancers.

Example 6

15 g of methylcellulose in the form of a liquid slurry is provided and is mixed with

| | |
|---|---|
| α-ketoglutaric acid | 6.000 g/l |
| N-acetyl-seleno-L-methionine | 1.5 mg/l |
| N-acetyl-L-methionine | 75 mg/l |
| KOH (85%) | 0.726 g/l |
| NaOH | 1.200 g/l |
| $NaH_2PO_4.2H_2$ | 16.00 g/l |
| $Na_2HPO_4.12H_2O$ | 6.00 g/l |
| 5-hydroxymethylfurfural | 1.000 g/l |

The resulting solution with a viscosity of 20-50 mPa·s and a pH value of about 6 was filled to 1 liter. It was then put up in portions of ¼ of a liter as enema packages and can serve preferably for the treatment of colon carcinoma at a daily dose of two enemas per day.

The therapeutic agent according to the invention can be used to fight all cancers and especially all virulent tumor pathologies which are associated with an increase in the alpha-ketoglutaric acid titre in the serum.

The use of the therapeutic agent according to the invention in the treatment of patients with malignant tumors of organs like the lungs, bronchia, breast tumors, tumors of the bladder, the stomach and the like which show increased blood levels of ketoglutaric acid as noted above, give rise to positive results in most cases after a treatment of several weeks. Thus after a treatment duration of one to two months in many cases, a state is reached in which the tumor which may have been clearly visible in X-ray can no longer be detectable and any metastasis which were associated therewith are effectively eliminated.

Of course the medication must be continued nevertheless so that a return of the cancer which can be then more difficult to treat, can be avoided. In such cases however the post treatment can be carried out with reduced daily doses so that for daily doses at the beginning of 3 to 30 g ketoglutaric acid and 1 to 5 g 5-hydroxymethylfurferal, the reduced doses of 3 to 9 g ketoglutaric acid and 0.5 to 1.5 g of 5-hydroxymethylfurfural are used. The treatment with the therapeutic agent according to the invention in the manner described has been found to afford improvement in the overall condition of the patient.

The duration of treatment differs based upon the extent to which the cancer has already progressed before treatment commences. It is desirable to start the treatment as soon as possible and most advantageously such that the cancer is in an early stage. Detrimental or even unpleasant side effects of the therapeutic agent, however, have not been observed.

I.) Example of Treatment According to the Invention with an Infusion Solution:

| | |
|---|---|
| α-ketoglutaric acid | 9.0 g/l |
| 5-hydroxymethylfurfural | 3.0 g/l |
| N-acetyl-seleno-L-methionine | 2.0 mg/l |
| N-acetyl-L-methionine | 100 mg/l |
| Glucose | 30.0 g/l |

$Na^+$ and $K^+$ to adjust the pH.

The infusion solution was put up in units of 0.5 l.

All of the patients were treated in the following manner.

At the beginning of the infusion treatment, for the first three days an infusion of 0.5 l was administered to each after the fourth day, each patient was treated with two infusions of 0.5 l with each infusion being administered for a duration of three hours. This type of administration was continued to the end of infusion therapy. The results at starting and after therapy were determined and analyzed by a computer tomogram and when necessary tumor markers were provided. In special cases (esophogeal carcinoma), the determinations were made by endoscopy.

Case 1: M.G., Female:

The patient had undergone an operation for breast cancer in 1975 and had an indication in 2001 of a return which was detected in connection with a pleural biopsy (mammary carcinoma reacher) which was associated with multiple bone metastasis in the trunk skeleton and liver metastasis of 2.1 to 1.1 cm in size.

These symptoms were treated with hormone therapy. The pathology developed further and in June 2002 a lymphangiosis cinamatosa as well as a lung embolism was diagnosed which was treated from June to October 2002 with polychemotherapy using Epirubicin and Taxotere. These treatments did not however lead to a regression of the disorder.

In November 2002, the patient, now classified as out of therapy, went to Dr. Ralph Herweg who examined the patient thoroughly. The liver metastasis was determined to be at the prominence of the liver and the rib metastasis on the $7^{th}$ and $9^{th}$ ribs at the right side. The lymphangiosis carcinomatosa was also still detectable. The illness was found by comparison to the prior examinations, to be progressing (examination report of Dr. E. Partl, Krankenhaus Kitzbuhel Hospital, the Laboratory of Dr. Schmoigl, Telfs). An indication thereof was among others the increase in the tumor marker CA 15-3 which was 55.4 U/ml on 20 Nov. 2002 and which had risen to 102.1 U/ml by 19 Dec. 2002.

On 9 Jan. 2003 infusion therapy was commenced. The daily treatment was continued to and including 7 Feb. 2003.

At that point using computer tomography (CT) there was no indication of hepatic metastasis, no induction of lung metastasis, no indication of rib metastasis and no reliable induction of active lymph angiosis carcinomatosa. The tumor marker CA 15-3, which had risen to 102.1 U/ml of 19 Dec. 2002 had dropped on 4 Feb. 2003 to 35 U/ml. There were no side effects, pain medication was not necessary and the patient was completely mobile.

Evaluation: Regression of the tumor pathology without an indication of residual tumor in the investigated region.

Subsequently a brain metastasis was detected which was treated on an outpatient basis by means of radiation therapy.

Case 2: H.I., 50, Female

Poorly differentiated uterine cancer G III, $N_x$ first diagnosis February 2000, subsequent abdominal hysterectomy and adnexectomy in June 2000. In January 2002 radiation therapy was begun and the series of radiation therapies varied for different regions:

In January 2002 radiation therapy was applied to the sacrum, in June 2002 radiation treatment began on the thoracic vertebra 12 (30 Gy), in October 2002 radiation therapy was applied to the right shoulder and in February 2003 radiation was done on the thoracic vertebral body 10. In May 2003 multiple lung metastases were detected. The radiation was interrupted because of the poor overall condition of the patient and on 9 Jun. 2003 treatment with the infusion according to the invention was undertaken. At the start there were numerous intrapulmonary metastasis between 5 and 13.5 mm, a liver metastasis of 14.5 cm in size, a bone metastasis in thoracicvertebra 12 (2.4 cm) a metastasis on the right side of the lumbar vertebra 5 (2.7 cm) as well as metastases to the lymph nodes in the neck. In addition The patient required 90 mg of Mundidol 3×1, 25 mg Vioxx 2×1, 8 ml of Vendal juice [opium] as required as a continuous pain medication. At the start the patient could only be transported in a recumbent state. The patient couldn't tolerate more than 10 minutes of sitting without pain. Therapy commenced on 9 Jun. 2003. Following therapy: Palpation clearly showed a regression of the tumor at the neck lymph nodes on the right side. Sonographically a regression of the liver metastasis was found (the marker legion had been shrunk to 7.9×5.1 cm). Mobility fully returned and the patient could fulfill all of her needs by herself.

The patient could stand for three hours a day and could shop by herself and even could visit her hairdresser. The pain medication following the treatment was:

Mundidiol 60 mg., 3×1, vendal juice, as required 2 ml.

Side effects were not present.

Case 3: F. J., 66, Male:

The patient had an esophageal cancer (eT3, cN1, Mx, GIII), In addition, the patient had diabetes mellitus type II that was difficult to treat and an arterial hypertonicity. At the start of the examination, a stenosed esophageal carcinoma between 30 and 35 cm in size running from the tooth arcade was detected. The cancer was a carcinoma in the Barett-esophagus. A weight loss of 10 kg was found for the patent and the patient had subjectively the feeling of illness. Mobility at the start was complete. No pain therapy was administered at the beginning.

On 13 Feb. 2003 the therapy according to the invention was commenced. Therapy ended for the first cycle on 13 Mar. 2003. Examination of the patient following therapy was carried out by gastroscope and showed a significant flattening of the previously ulcerized and growing carcinoma. Also there was a significant weight gain and the patient subjectively felt very well. There were no limitations on the mobility of the patient. Pain medication was not necessary and no side effects were observed.

Evaluation

Retroregression of the illness improvement of the overall condition of the patient, subjectively significant improvement of the patient's general feelings. After 13 Mar. 2003 the patient was treated with an alphaketoglutaric acid/5-hydroxymethylfurfural beverage.

A further treatment cycle was carried out from 12 May 2003 through 17 May 2003. Additionally 1200 mg of 5-fluouracil was administered.

Evaluation

In a new check by means of endoscopy a further regression of the tumor was found as seen intraluminally. The check showed an absence of stenosis and no swallowing difficulties. The body weight of the patient returned to its starting level before the weight loss. Histological monitoring showed a downstaging to G II-III and endosonographically, a regression to the eT2-3 state. The lymph node metastases which had previously appeared in CT were no longer detectable. An interesting point was that at no point in time was there a bone marrow deterioration as a result of the additional chemotherapy.

Case 4, B.E. 76, Female

The patient was diagnosed with bladder carcinoma (pT4, N2=enlarged lymph nodes, M 1=remote metastasis GIII) with blocked right kidney.

The patient desired the above described therapy. A bladder biopsy for histological purposes was taken on 4 Feb. 2003 at the University Clinic in Innsbruck, Austria and showed a muscle-invasive bladder carcinoma of at least P2 with carcinoma in situ N2, Mx, GIII with respect to right side hydro nephrosis (kidney blockage at the right side as a result of the tumor, a kidney stent (splint) was introduced on 17 Mar. 2003 (University Clinic, Innsbruck).

On 19 Mar. 2003 infusion treatment with the therapeutic agent of the invention was begun.

Starting examination: Cytoscopically clear tumor masses were detected which had grown into the urinary bladder, the splint on the right side was found in place. The right osteum (urinary opening in the bladder wall) could not be verified. Sonographically it was also observed that the tumor had a size of 3.5×2 cm in the region of the osteum. There was also an infiltration of the uterus and a possible infiltration of the rectum. In addition a space shift to the left from the center line of 5.3 cm was observed. At the beginning no pain therapy was applied and mobility was complete.

On 19 Mar. 2003 the infusion therapy was begun. The infusion according to the invention was administered from 19 Mar. 2003 to 6 Apr. 2003 and from 8 Apr. 2003 to 20 Apr. 2003. Following the therapy, cytoscopic investigation of the tumor showed a significant regression. The urine passage was clearly visible and the remaining bladder wall free from growths. Sonographically, a return of the space in the region of the osteum could be established. A biopsy of the lymph nodes in the left branch showed sclerotic binding tissue with focused infiltration by solids or single-cell infiltrating polymorphic cell complexes of the aforedescribed slightly differentiated bladder carcinoma. The presence of sclerotic tissue in the lymph nodes was an indication of tumor reduction by chemotherapy. In a CT examination on 2 May 2003 (University of Innsbruck) a significant regression of a modular tumor manifestation at the lymph nodes from 5.5 to 4.9 cm was confirmed. The urinary bladder wall was found to be somewhat more prominent in the context of a high precision measurement. Newly developed lymph node enlargement para-aortally and interaortocavally (maximum 1.7 cm) as measured were found to be only in the process of development. The regression of the tumor manifestation in the region of the osteum was also here noted. Further examination showed no bone metastases. As a general matter this CT indicated a regression of the pathology. Mobility was completely restored upon discharge. No pain medication was required after discharge and there were no after effects.

Regression was found along with the histological indication of lymph node sclerosis [sicatrization].

Case 5: O. H. 65, Female

This patient involved a metastatic mammary carcinoma with liver metastases, lung metastases, malignant, pleural effusion, aszites, leukopenia, thromopenia and blood vessel damage with the beginning of liver breakdown. After multiple polychemotherapy treatments, shortly before the commencement of therapy with the infusion solution according to the invention therapy resistant aplasia and blood vessel damage developed. An oxygen substitution (4 l/min) in the case of respiratory insufficient following the last chemotherapy/ cycle was required. Azites and pleural effusion were not of a point type with respect to the aplasia. The patient was immobile and bed ridden.

From 7 Feb. 2003 to 6 Mar. 2003 a treatment with the infusion solution according to the invention was carried out. Then is the patient was subsequently treated with an alpha-ketoglutaric acid/5-hydroxymethyl furfural beverage solution (orally). Thereafter the afore described liver metastases were no longer detectable (by sonography at the Kitzbuehel Hospital). The pleural effusion and the azites were clearly suppressed and no longer a problem. The oxygen substitution itself was no longer necessary. Radiological examination indicated a clear improvement of the pulmonary situation (as found by Dr. E. Partl) of the Kitzbühel Hospital). A more rapid increase of the hematalogical parameters including a rapid increase in thrombosis was detectable. The patient was completely mobile on leaving the hospital.

Case 6: P. P., 62, Male:

Metastatic bronchial carcinoma, multiple lung metastasis and lymph node metastases, lung function restrictions.

At the beginning there was a clear respiratory insufficiency but no pain of therapy and complete mobility.

The therapy was carried out with the infusion solution according to the invention from 13 May 2003 through 13 Jun. 2003. As a result there was regression of the spatial demand (the lymph node metastases) at the right side and the remaining tumor mass was stable. There was a clear improvement of the overall condition of the patient, an improvement in the ability to tolerate exertion (expanded walks and swimming possibilities). Mobility upon discharge was complete, no pain medication was required and there was no side effects. The tumor mass showed in total about a 50% regression (CT Dr. E. Partl, Kitzbuhel Hospital).

Conclusion:

A regression of the cancer, improvement in the general state of the patient and subjectively a clear improvement in the feeling of well being.

II. Case Studies with a Treatment According to EP 326 826 B1

Composition of the Therapeutic Agent Using:

a) Infusion solution with a volume of 0.5 liter containing.

| | |
|---|---|
| Alpha-ketoglutaric acid | 3.0 g |
| 5-hydroxymethylfurfural | 1.0 g |
| glucose | 25.0 g |
| Sodium ion | 35.0 mmol |
| potassium ion | 10.0 mmol |
| calcium ion | 4.0 mmol |
| magnesium ion | 2.0 mmol |
| zinc ion | 0.0365 mmol |
| phosphate ion | 20.0 mmol |
| chloride ion | 8.0 mmol | b) infusion solution with a volume of 1 liter containing

| | |
|---|---|
| Alpha-ketoglutaric acid | 6.0 g |
| 5-hydroxymethylfurfural | 2.0 g |
| glucose | 50.0 g |
| Sodium ion | 70.0 mmol |
| potassium ion | 20.0 mmol |
| calcium ion | 8.0 mmol |
| magnesium ion | 4.0 mmol |
| zinc ion | 0.073 mmol |
| phosphate ion | 20.0 mmol |
| chloride ion | 16.1 mmol | c) Preparation for oral administration in the form of a beverage granulate with a portion bag containing

| | |
|---|---|
| Alpha-ketoglutaric acid | 0.75 g |
| 5-hydroxymethylfurfural | 0.125 g |
| Zno | 5.0 mg |
| Sifted sugar | 3.007 g |

The patients received an infusion of 1 liter or 0.5 liters per day. The administration was carried out daily and on the weekend when no infusion was administered, the oral preparation replaced it.

Case 7: H.C., Female. 1908:

Diagnosis: Carcinoma of the right breast. 1986 palliative mastectomy including removal of the breast wall muscle. In an examination on 16 Jan. 1987 of the right axilla, a swollen lymph node was detected.

Following this diagnosis, the patient turned to a doctor who had been engaged in administering in a series of tests the infusion solution of EP 326,826 to out therapy patients.

Since this patient was apparently becoming weaker and weaker and suffered weight loss, and was already bed-ridden, from 18 May 1987 she was treated per day with 0.5 l of the above-mentioned infusion solution (a). After six infusions, she was able to stand and the size of the lymph node was reduced. After a total of 14 infusions, the patient was converted to further treatment with the oral preparation©). This preparation was prescribed 3× daily for a period of 6 months.

On 4 Dec. 1987, the patient was radiologically examined. Both in the region of the lungs and the armpit no enlarged lymph nodes were observed any longer. Thus at this point in time a good prognosis was predicted.

In the year 1988, however, two small focii were found in the operation scar tissue. These focii were removed in an operation in the same year. On 10 May 1989, a tumor was discovered on the still-present left breast. It was removed on 20 May 1989 and it was determined to be benign. No further traces of the original virulence were found.

Case 8: B.L., Female, 1912:

This patient was also diagnosed with a breast cancer with lymphoma. In addition, liver metastasis were also found.

On 31 Mar. 1989 treatment was begun with by infusion with the experimental infusion solution (b). This treatment led to alleviation of pain although the patient simultaneously developed is an increasingly strong yellow coloration so that the treatment was interrupted on 14 Apr. 1989. The patient died on 29 Apr. 1989.

Case 9: H. F., Male, 1926:

The patient had an invasive ductal mammary carcinoma on the right side (pT 4 BGM0, No) and a modified radical mastectomy right as well as an axillary lymphadenectomy on 13 Feb. 1987, one after the other. An epigastric sonograph following surgery and a full-body skeletal scintography showed no indication of metastasis.

Because of all of the problems, the patient was subjected to thorax-wall radiation and after the fifth radiation treatment the patient was found to be symptom free. The lymph nodes were considered to have a good prognosis (4 Apr. 1987). In an x-ray examination on 18 Aug. 1987, a painful extensive collection of fluid was visible in the right pleural space. On 29 Sep. 1987, for the first time, skeletal metastasis was acknowledged, which led to pain in the right chest cavity, pain in the region of the lumbar vertebral column and pain in the region of the left hip.

On 3 Oct. 1987, infusion therapy with the infusion solution a) was commenced initially at home and from 5 Oct. 1987, daily by prescription. On 7 Oct. 1987 the metastases to the lumbar vertebral column were checked. Multiple small osteologic destructive focii were found in practically all lumbar vertebral bodies. Further multiple small-flake osteological destructive focii were found in the region of the heads of both femurs as well as in the necks of the leg bones. The infusion was repeated in spite of these findings. There was no significant change in the metabolism or general condition. Up to 19 October the patient had 11 infusions. The therapy was modified at this stage because of the confused state of the patient and because of spontaneous fractures. On 26 October the presence of brain metastasis was detected. On 30 Oct. 1987 the patient died.

Case 10: K. R., Male 1925

The patient had an inoperable bronchial carcinoma in the right underlapped brobatoria, massive lymph node involvement in the entire media stinum and infiltration in the pericardium (heart sac) and in the esophagus. The patient came from thorax treatment. Infusion commenced on 11 Aug. 1987 with infusion solution b), B. P. 75/115, 3.0 million erythrocyte and 10.5 Hb count. The patient had multi lobular pain and was taking Temgesic. He also suffered from muscle cramps. On 24 August, after the 8$^{th}$ infusion, the patient responded to an inquiry to be effect that he felt "super". Whether the various metastases had receded was not examined since after the brief course of therapy a recession could hardly be expected. The infusion was continued until 7 Sep. 1987. There were 19 infusions. At the request of relatives the infusion therapy was interrupted and the patient brought to the hospital of the Barmherzigen Brothers where the patient died on 23 Sep. 1987. This showed that the infusion therapy improved the general condition of the patient but the massive involvement of the phosii throughout the body namely the lymph nodes and the media stinum hardly could be overcome since the infusion therapy was interrupted.

Discussion of the Case Studies:

The six case studies of Part I have in all cases the surprising effect that the treatment involved exclusively out of therapy patients and thus an advanced process for a variety of different metastasis.

If one considers for example case study 1 of a female patient who had already been operated upon in 1975 for mammary carcinoma and who in 2002 and had indications of a return in the form of *Pleurotus* carcinoma tosa with rapid involvement of the liver and bones in the form of liver and bone metastasis and which could not be attacked by chemotherapy, the case of the patient can be seen to be very special. All of these massive features of the progressive pathology were so intensively attacked by one month of continuous fusion treatments according to the invention that in examination by a tomogram as part of the examination after therapy not only could not the lymph node involvement not be detected any longer but also the liver metastases and the multiple bone metastases in the basic skeleton could not be detected. Correspondingly, the mobility and general well being of the patient were very good. This patient would not have been responsive to a therapy in EP 326 826 B1 because such therapy is ineffective for liver and bone metastasis. (See the case study 8).

The same situation, also in the case of bone metastasis which cannot be attacked by the infusion by EP 326 826 B1. This can be seen clearly in case study 9 where no bone metastasis was apparent over a long period of time. The infusion treatment was there first commenced when the metastasis was noted. The infusion treatment was begun only four days before the diagnosis of bone metastasis in the lumbar vertebral column. In spite of the further treatment the bone metastasis spread rapidly. Ten days before the death of the patient the infusion therapy was begun, the treating practitioner extended this therapy only because the general condition improved that the bone metastasis would not be attacked was apparently clear to him. The fact that with the solution liver and bone metastasis can be attacked and even eliminated, something which does not occur with the previously known solution is not limited to mammary carcinoma as will be apparent form case study 6 which deals with bronchial cancer. By contrast, from case study 10 it will be apparent that patients who also have a bronchial carcinoma can be treated not only in those cases where the infusion therapy according to EP 326 826 B1 may lead to a general improvement of the well being, but also in cases of massive involvement with focii of the pathology to not only limit development but even to eliminate them.

The invention claimed is:

1. A therapeutic agent which comprises as therapeutically effective ingredients: alpha-ketoglutaric acid or its pharmaceutically effective salts and 5-hydroxymethyl-furfural promoting azomethine formation in an enzyme independent reaction, whereby the mass ratio of the ketoglutaric acid to the 5-hydroxymethyl-furfural is greater than 1:1 and wherein the therapeutic agent contains as further therapeutically effective ingredients: N-acetyl-seleno-L-methionine and N-acetyl-L-methionine whereby the latter is present in excess with respect to the former, in an amount sufficient to suppress uptake of the N-acetyl-seleno-L-methionine into body tissues.

2. The therapeutic agent according to claim 1 characterized in that the mass ratio of alpha-ketoglutaric acid to N-acetyl-seleno-L-methionine is 100:1 to 20000:1.

3. The therapeutic agent according to claim 1 wherein the mass ratio of N-acetyl-L-methionine to N-acetyl-seleno-L-methionine is 20:1 to 300:1.

4. The therapeutic agent according to claim 1 wherein it further comprises glucose, fructose or a mixture thereof.

5. The therapeutic agent according to claim 1, wherein it is put up in an aqueous solution and the N-acetyl-seleno-L-methionine is present in an amount of 1.4 to 2.3 mg/l and the N-acetyl-L-methionine is present in an amount of 70 to 230 mg/l.

6. The therapeutic agent according to claim 4 wherein it contains an electrolyte from the group of sodium or potassium.

7. The therapeutic agent according to claim 1 wherein it is administered intravenously and has a pH value of 4 to 6.

8. The therapeutic agent according to claim 4 or claim 6 wherein the alpha-ketoglutaric acid is present in a concentration of 3 to 20 g/l, the 5-hydroxymethylfurfural is present in a concentration of 1 to 3 g/l, the glucose is present in a concentration of 20 to 100 g/l, the sodium ion is present in a concentration of 60 to 160 mmol/l and the potassium ion is present in a concentration of 15 to 40 mmol/1.

9. The therapeutic agent according to claim 8 wherein the alpha-ketoglutaric acid is present in a concentration of 6 to 16 g/l, 5-hydroxymethylfurfural is present in a concentration of 1 to 2.5 g/l, the glucose in a concentration of 20 to 50 g/l, the sodium ion in a concentration of 70 to 160 mmol/l and the potassium ion is present in a concentration of 20 to 40 mmol/1.

10. The therapeutic agent according to claim 1 which is put up in a solid or liquid or oral or rectal administration dosage form which contains the ketoglutaric acid at least in part in the form of a monosodium or monopotassium salt thereof.

11. The therapeutic agent according to claim 10 which further comprises a lubricating agent and/or extender and/or a taste improving disaccharide.

12. The therapeutic agent according to claim 10 which comprises in the dosage unit 3 to 9 g of alpha-ketoglutaric acid, 0.5 to 1.5 g 5-hydroxymethyl-furfural, 1.4 to 2.3 mg N-acetyl-seleno-L-methionine and 70 to 230 mg of N-acetyl-L-methionine.

13. A method of making a therapeutic agent in a form suitable for intravenous administration according to claim 7 wherein the alpha-ketoglutaric acid is dissolved at elevated temperature in distilled water which has had its oxygen content reduced by a gasification and glucose or fructose added to it together with alkalies other than ammonia or amines, the pH being adjusted to be in a range of 4 to 6 and N-acetyl-seleno-L-methionine, N-acetyl-L-methionine and the 5-hydroxymethyl-furfural are added.

14. A method of making a preparation suitable for oral or rectal administration according to claim 10 wherein to adjust the pH from 3 to 6 the ketoglutaric acid is partly to entirely used in the form of its monosalt with sodium and/or potassium and in which extenders and if desired also disaccharides are mixed therewith and to this mixture the 5-hydroxymethyl-furfural, the N-acetyl-seleno-L-methionine and the N-acetyl-L-methionine are added whereupon the mixture is put up in the desired form of administering as a particle, granulate, in tablets, or in an irrigating liquid.

15. A cytocidal method of treating a malignant breast, uterine, esophageal, bladder or lung tumor in a patient afflicted with said malignant tumor which comprises the step of administering to said patient, an amount of the therapeutic agent defined in claim 1, effective to treat the malignant tumor by suppressing angiogenic activity of the tumor.

16. The cytocidal method of treating a malignant tumor defined in claim 15 wherein the therapeutic agent is administered to the patient orally, rectally, in the form of an irrigation, or as an intravenous infusion.

17. The cytocidal method of treating a malignant tumor defined in claim 16 wherein the therapeutic agent is administered to the patient as an intravenous infusion.

18. A therapeutic agent administrable as an intravenous infusion, which consists essentially of:
 alpha-ketoglutaric acid 3-20 g/l
 5-hydroxymethylfurfural 1-3 g/l
 N-acetyl-seleno-L-methionine 1.4-2.3 mg/l
 N-acetyl-L-methionine 70-230 mg/l
 glucose 20-100 g/l
 sodium ion 60-160 mmol/l and
 potassium ion 15-40 mmol/l
 in combination with a pharmaceutically acceptable inert carrier suitable for intravenous administration.

19. A cytocidal method of treating a malignant breast, uterine, esophageal, bladder or lung tumor in a patient afflicted with said malignant tumor which comprises the step of administering to said patient, by intravenous infusion, an amount of the therapeutic agent defined in claim 18, effective to treat the malignant tumor by suppressing angiogenic activity of the tumor.

20. The therapeutic agent administrable as an intravenous infusion, defined in claim 18 wherein the alpha-ketoglutaric acid is present in an amount of 9.0 g/l; the 5-hydroxymethylfurfural is present in an amount of 3.0 g/l; the N-acetyl-seleno-L-methionine is present in an amount of 2.0 mg/l; and the N-acetyl-L-methionine is present in an amount of 100 mg/l.

21. A cytocidal method of treating a breast, uterine, esophageal, bladder or lung carcinoma in a patient afflicted with said carcinoma which comprises the step of administering to said patient, by intravenous infusion, an amount of the therapeutic agent defined in claim 20, effective to treat the carcinoma by suppressing angiogenic activity of the carcinoma.

* * * * *